United States Patent
Shirasaka et al.

(10) Patent No.: US 11,589,791 B2
(45) Date of Patent: Feb. 28, 2023

(54) MEASURING APPARATUS, ELASTIC MEMBER, AND INPUT BOX

(71) Applicant: NIHON KOHDEN CORPORATION, Tokyo (JP)

(72) Inventors: Shogo Shirasaka, Tokorozawa (JP); Norihide Shimizu, Tokorozawa (JP); Takanori Sato, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 989 days.

(21) Appl. No.: 16/383,983

(22) Filed: Apr. 15, 2019

(65) Prior Publication Data
US 2019/0320922 A1  Oct. 24, 2019

(30) Foreign Application Priority Data

Apr. 23, 2018 (JP) .............................. JP2018-082428

(51) Int. Cl.
*A61B 5/145* (2006.01)
*A61B 5/24* (2021.01)

(52) U.S. Cl.
CPC .... *A61B 5/2415* (2021.01); *A61B 2560/0406* (2013.01); *A61B 2560/0468* (2013.01)

(58) Field of Classification Search
CPC ............ G01N 27/3272; G01N 27/3273; B01L 3/502715; A61B 5/14532
See application file for complete search history.

(56) References Cited

U.S. PATENT DOCUMENTS

2008/0249383 A1* 10/2008 Sass .................... A61B 5/6849
600/345
2017/0290535 A1* 10/2017 Rao .................... A61B 5/1473

FOREIGN PATENT DOCUMENTS

| JP | H09-266899 A | 10/1997 |
| JP | 2001-238862 A | 9/2001 |
| JP | 2004-081234 A | 3/2004 |
| JP | 2013-099497 A | 5/2013 |

OTHER PUBLICATIONS

Nihon Kohden Corporation, "Neuropack X1 EP/EMG/NCV Measuring System MEB-2300 Desktop System", https://us.nihonkohden.com/media/1066/meb-2300-brochure_nmlb-27c-co-02162.pdf, 2012.
Japanese Office Action dated Jan. 4, 2022 issued in Japanese Patent Application No. 2018-082428.

* cited by examiner

Primary Examiner — Michael J D'Abreu
(74) Attorney, Agent, or Firm — Pearne & Gordon LLP

(57) ABSTRACT

A measuring apparatus is configured to be connected to an electrode to measure biopotential. The measuring apparatus has an input box to which the electrode is connected. The input box has a tubular elastic member configured to hold a cap to be mounted on the electrode, and an insertion portion configured such that the elastic member is insertable into the insertion portion. The elastic member has an entrance having a first inner diameter and a contracted portion having a second inner diameter smaller than the first inner diameter.

13 Claims, 5 Drawing Sheets

MEASURING APPARATUS, ELASTIC MEMBER, AND INPUT BOX

CROSS-REFERENCE TO RELATED APPLICATION

The present application claims priority to Japanese Patent Application No. 2018-082428 filed on Apr. 23, 2018 the entire content of which is incorporated herein by reference.

BACKGROUND

The presently disclosed subject matter relates to a measuring apparatus, an elastic member, and an input box.

In acquiring biopotential of a subject using a needle electrode, a medical personnel may need to hold the needle electrode with a hand when, for example, it is between measurements. This is inconvenient as the medical personnel can use only the other hand during a measurement work.

When mounting a cap on a needle portion of the needle electrode after its use, care has to be taken so that blood left on the needle does not contact the cap.

In view of this, an electrode connection box may be provided with a holder to hold a needle electrode. Neuropack X1 is a related art product of Nihon Kohden. See, e.g., https://us.nihonkohden.com/media/1066/meb-2300-brochure_nmlb-27c-co-02162.pdf.

However, caps have a variety of shapes. The holder is made of a hard resin or the like, the same material as a housing of the connection box. Therefore, the elastically deformable range of the holder is small. When a shape of the cap for the needle electrode does not match a shape of an opening of the holder, the needle electrode on which the cap is mounted cannot be held in the holder, in which case the medical personnel may need to hold the needle electrode in a hand during the measurement.

SUMMARY

Illustrative aspects of the presently disclosed subject matter provide a measuring apparatus, an elastic member, and an input box, with which an electrode cap can be held irrespective of a shape of the electrode cap.

According to an illustrative aspect of the presently disclosed subject matter, the measuring apparatus includes a tubular elastic member configured to hold a cap to be mounted on the electrode, and an insertion portion configured such that the elastic member is insertable into the insertion portion. The elastic member includes an entrance having a first inner diameter and a contracted portion having a second inner diameter smaller than the first inner diameter.

According to an illustrative aspect of the presently disclosed subject matter, the elastic member has a tubular shape and is configured to hold a cap that protects an electrode used with a measuring apparatus. The elastic member includes an entrance having a first inner diameter and a contracted portion having a second inner diameter smaller than the first inner diameter.

According to an illustrative aspect of the presently disclosed subject matter, the input box is configured such that an electrode used with a measuring apparatus is connected to the input box. The input box includes a tubular elastic member configured to hold a cap to be mounted on the electrode, and an insertion portion configured such that the elastic member is insertable into the insertion portion. The elastic member includes an entrance having a first inner diameter and a contracted portion having a second inner diameter smaller than the first inner diameter.

DETAILED DESCRIPTION

Hereinafter, an embodiment of the presently disclosed subject matter will be described in detail with reference to the drawings.

In the description, a "left-right direction", a "front-rear direction", and a "up-down direction" will be used for the purpose of illustration. These directions are relative directions defined with respect to an input box 4 and an elastic member 6 illustrated in FIGS. 2 to 5. The "up-down direction" includes an "upper direction" and a "lower direction". The "front-rear direction" includes a "front direction" and a "rear direction". The "left-right direction" includes a "left direction" and a "right direction".

Figure 1:
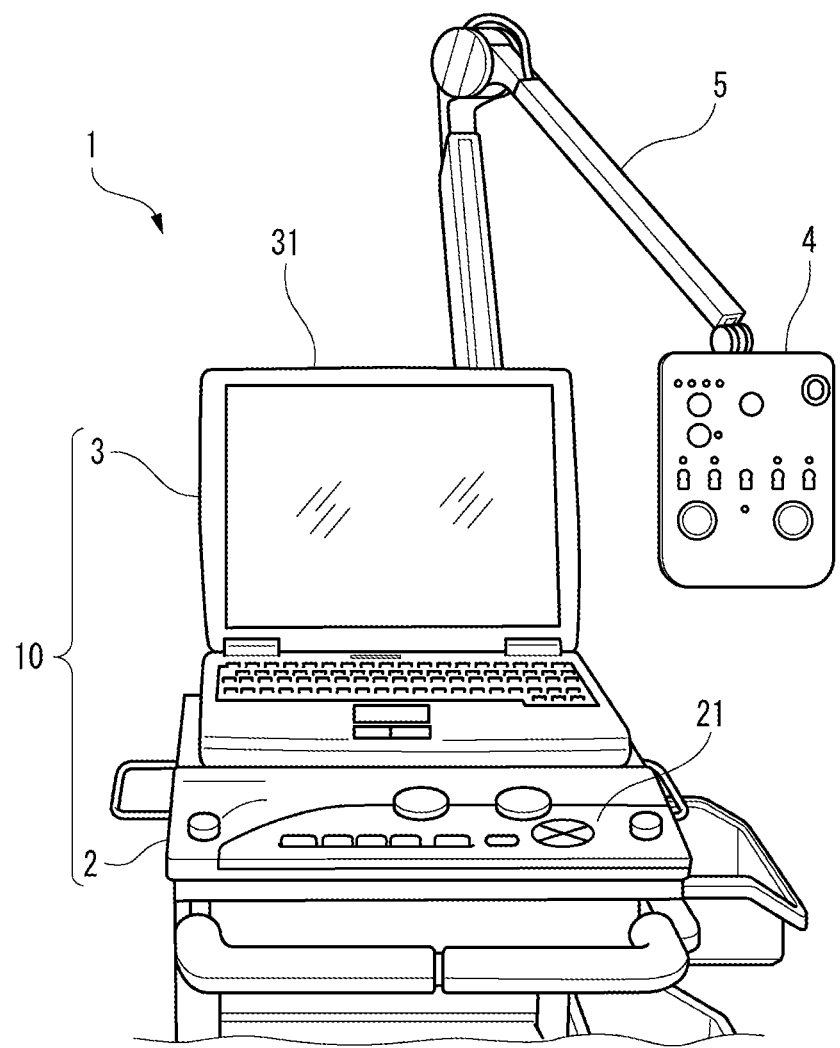
FIG. 1 illustrates a measuring apparatus according to an embodiment of the presently disclosed subject matter.

FIG. 1 illustrates a measuring apparatus 1 according to an embodiment of the presently disclosed subject matter. As illustrated in FIG. 1, the measuring apparatus 1 includes a main unit 10, the input box 4, and a connection portion 5. The main unit 10 includes an operation terminal 2 and a display terminal 3. The measuring apparatus 1 is, for example, connected to a needle electrode 7 to measure biopotential.

The operation terminal 2 includes one or more processors and one or more memories. Examples of the processor include a CPU, an MPU, and a GPU. The processor may include a plurality of processor cores. Examples of the memory include a ROM and a RAM. The ROM may store various programs to be executed by the processor. The RAM includes a plurality of work areas in which the various programs to be executed by the processor are stored. For example, the processor designates at least a part of the program stored in the ROM, develops the program on the RAM, and cooperates with the RAM to execute various processes.

The operation terminal 2 includes an operating portion 21. The operating portion 21 receives various input operation of a medical personnel. The various input operation includes operation for measuring biopotential of a subject and analyzing biological information of a subject, operation for displaying the biological information or an analysis result on the display terminal 3, or the like. The operation terminal 2 processes, based on operation of the medical personnel, the biological information transmitted from the input box 4. Examples of processing contents include high-pass filter processing, low-pass filter processing, AC filter processing, sensitivity change, average addition processing. The operation terminal 2 transmits processed biological information to the display terminal 3.

The display terminal 3 is, for example, an electronic device such as a desktop PC, a notebook PC, a tablet terminal. The display terminal 3 includes a display 31 for displaying the biological information transmitted from the operation terminal 2. The display 31 is, for example, a display such as a liquid crystal display or an organic EL display. The display 31 can display various biological information such as waveform data and measurement data.

The display terminal 3 includes a processor and a memory similar to those of the operation terminal 2. For example, the processor designates at least a part of the program stored in the ROM, develops the program on the RAM, and cooperates with the RAM to execute various processes. The display terminal 3 can store the biological information received from the operation terminal 2 or other measuring apparatuses. The stored biological information is transmitted to, for example, a printer (not illustrated) connected to the measuring apparatus 1.

The input box 4 is, for example, an electrode connection box. An measurement electrode or the like may be connected to the input box 4. The input box 4 can be mounted on the main unit 10 via the connection portion 5. The connection portion 5 is, for example, a movable arm. The input box 4 is connected to the operation terminal 2 in a communicable manner.

Figure 2:
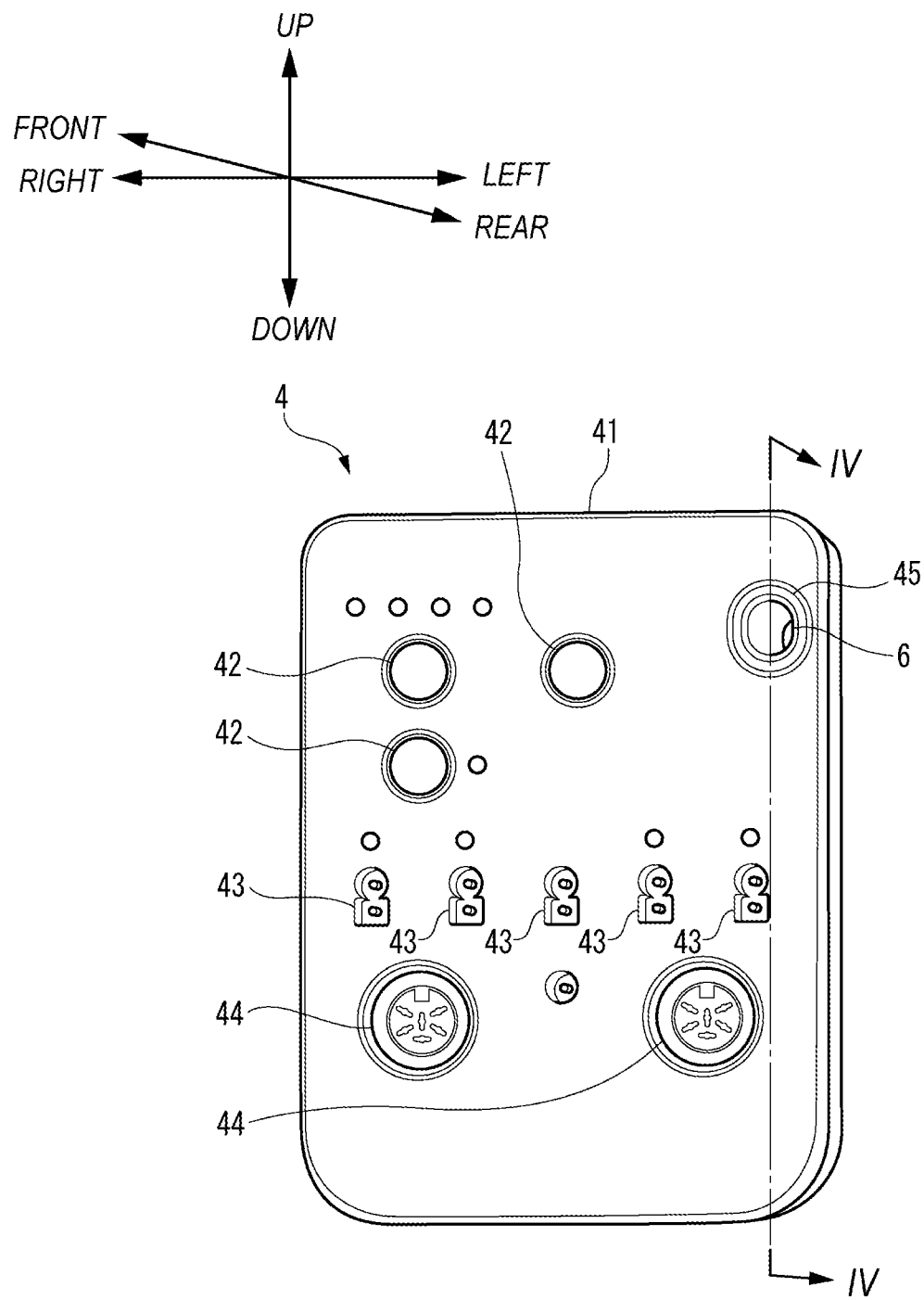
FIG. 2 is a perspective view of an input box according to an embodiment of the presently disclosed subject matter.

FIG. 2 illustrates the input box 4 according to the embodiment of the presently disclosed subject matter. As illustrated in FIG. 2, the input box 4 includes a housing 41, a switch 42, a first connector 43, a second connector 44, and an insertion portion 45.

The housing 41 is substantially rectangular. Each of four corners of the housing 41 has an arc-shaped curved surface. The housing 41 is, for example, formed of resin. The switch 42, the first connector 43, the second connector 44, and the insertion portion 45 are provided on a front surface of the housing 41. The insertion portion 45 is a through hole and extends to a rear surface of the housing 41. In contrast, the switch 42, the first connector 43, and the second connector 44 are not provided on the rear surface of the housing 41.

The first connector 43 and the second connector 44 are connectors for enabling connection between the input box 4 and an electrode.

The insertion portion 45 is a through hole. An opening at each end of the insertion portion 45 is preferably elliptic or oval, but may be any other shape. A circumferential length of the insertion portion 45 is slightly larger than a circumferential length of the elastic member 6, so that the elastic member 6 can be inserted. The insertion portion 45 is provided at the upper left side of the input box 4 in the present embodiment, but the presently disclosed subject matter is not limited to this example. The insertion portion 45 may be provided at other positions of the input box 4.

Figure 3:
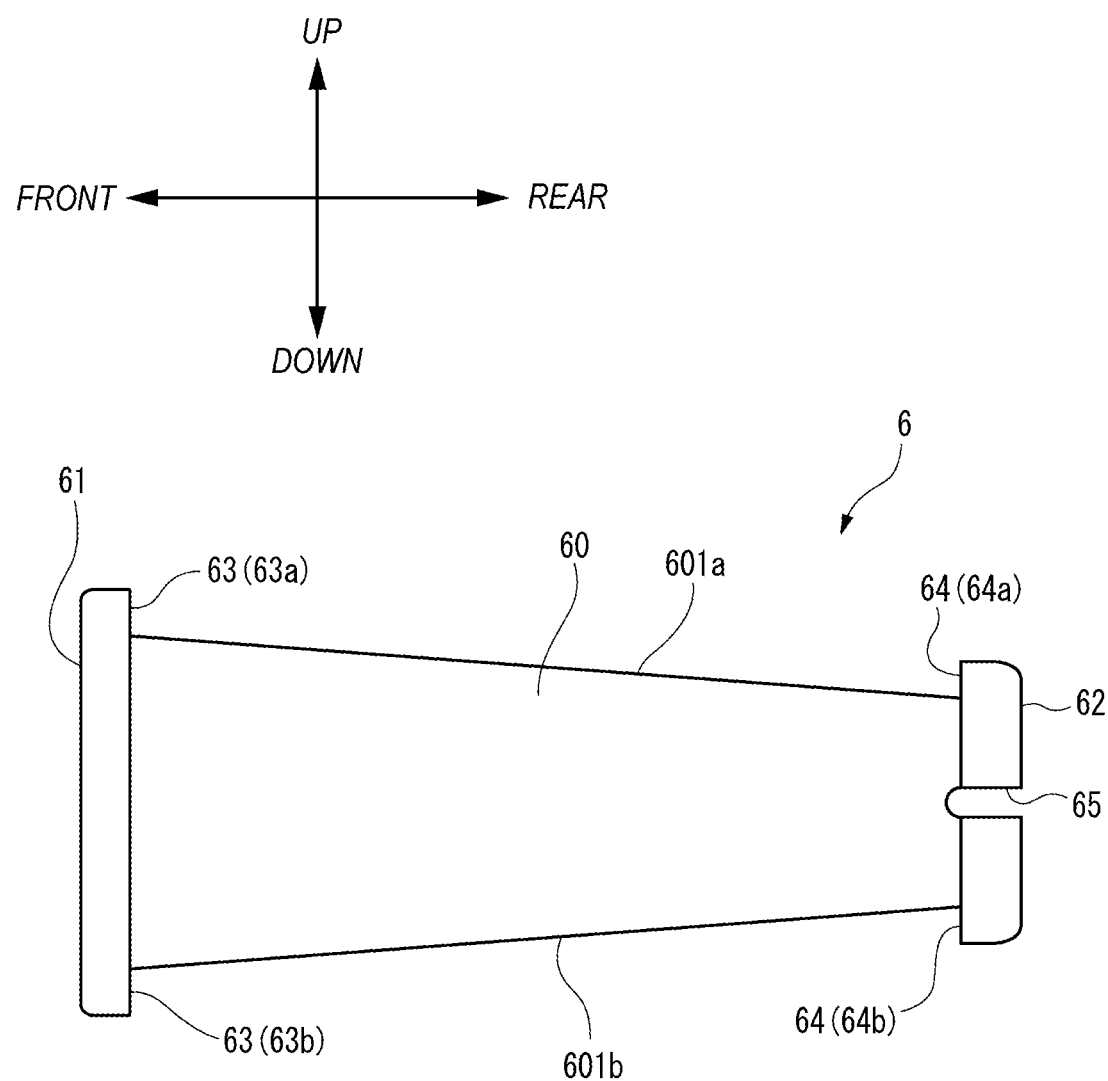
FIG. 3 is a side view of an elastic member according to the embodiment of the presently disclosed subject matter.

FIG. 3 is a side view of the elastic member 6 according to one embodiment of the presently disclosed subject matter. As illustrated in FIG. 3, the elastic member 6 includes a tubular body 60, a first opening portion 61, and a second opening portion 62. The elastic member 6 has a tubular shape. The elastic member 6 is formed of an elastic material such as silicone.

The tubular body 60 is configured such that its outer diameter becomes smaller toward its rear end. The entire circumferential surface of the tubular body 60 is configured as a tapered surface. The tubular body 60 has a plurality of inner diameters different in length. When the shape of the tubular body 60 is viewed from a lateral side, an outline 601a on the upper side of the tubular body 60 is inclined downward toward the rear, and an outline 601b on the lower side of the tubular body 60 is inclined upward toward the rear, thereby forming a vertically symmetrical shape.

The first opening portion 61, which is an entrance side of the elastic member 6, is provided at the front end of the elastic member 6. A first rim 63 is formed at the first opening portion 61, and extends outward in a radial direction of the first opening 61. An outer diameter of the first opening portion 61 is larger than the maximum outer diameter of the tubular body 60. The first rim 63 may function as an engagement portion 63a that can be engaged with the insertion portion 45.

The second opening portion 62 is located at an opposite side of the entrance of the elastic member 6, and is provided at the rear end of the elastic member 6. A second rim 64 is formed at the second opening portion 62, and extends outward in a radial direction of the second opening portion 62. An outer diameter of the second opening portion 62 is larger than the minimum outer diameter of the tubular body 60, and is smaller than the outer diameter of the first opening portion 61. The second rim 64 may function as an engagement portion 64a that can be engaged with the insertion portion 45.

Further, a slit 65 is formed in the second opening portion 62. The slit 65 extends, from a substantial center of the second opening portion 62, in a front-rear direction. Therefore, the medical personnel can easily squeeze the second opening portion 62 by applying an inward force in an up-down direction of the second opening portion 62 to the second rim 64.

The slit 65 is formed in the second opening portion 62 in the present embodiment, but the presently disclosed subject matter is not limited to this example. The slit 65 may be formed in the first opening portion 61. Alternatively, the slit 65 may be formed in both the first opening portion 61 and the second opening portion 62.

Figure 4:
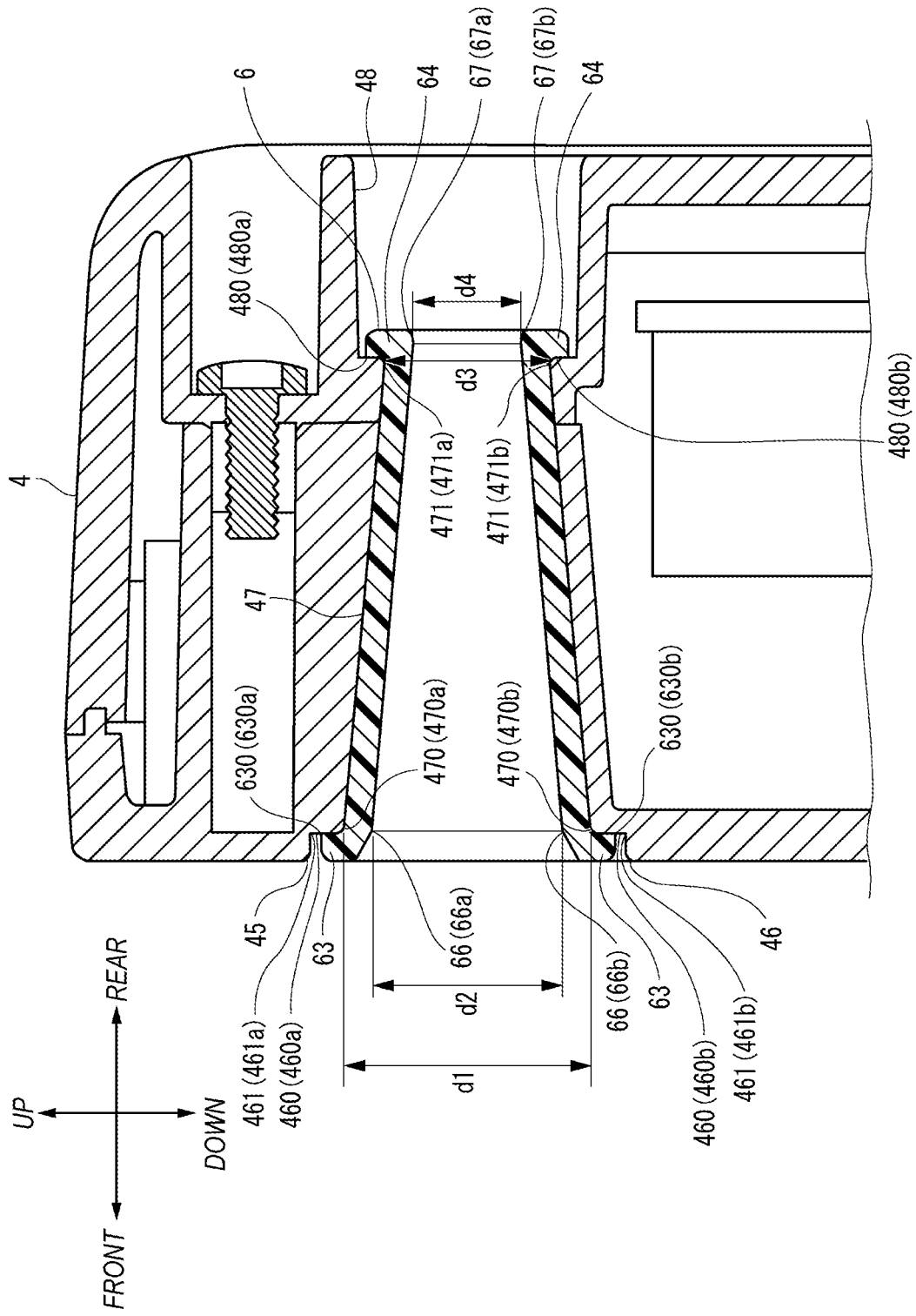
FIG. 4 is a cross-sectional view taken along the line IV-IV in FIG. 2.

FIG. 4 is a cross-sectional view taken along the line IV-IV in FIG. 2. As illustrated in FIG. 4, the insertion portion 45 includes a first portion 46, a second portion 47, and a third portion 48. The first portion 46 is an inner circumferential surface of the insertion portion 45 located at the entrance side of the insertion portion 45. When the elastic member 6 is inserted into the insertion portion 45, the first portion 46 is located at the front side of the first rim 63. The second portion 47 is located at the rear side of the first rim 63 and the front side of the second rim 64. The third portion 48 is located at the rear side of the front surface of the second rim 64. The first portion 46, the second portion 47, and the third portion 48 are contiguous with each other. An inner diameter of a rear end portion of the first portion 46 is larger than an inner diameter of a front end of the second portion 47. Therefore, first receiving portions 460 (460a, 460b) are formed at the rear end of the first portion 46. In addition, an inner diameter of a front end of the third portion 48 is larger than an inner diameter of a rear end of the second portion 47. Therefore, second receiving portions 480 (480a, 480b) are formed at the front end of the third portion 48.

An inner diameter of the second portion 47 is reduced rearward. The second portion 47 in the entire circumferential direction is a tapered surface. A reduction ratio of the inner diameter of the second portion 47 is substantially the same as a reduction ratio of the outer diameter of the tubular body 60. An inner diameter $d_1$ connecting entrance end portions 470 (470a, 470b) of the second portion 47 is larger than an inner diameter $d_3$ connecting rear end portions 471 (471a, 471b) of the second portion 47. In addition, the elastic member 6 has a thickness. Therefore, the inner diameter $d_2$, which corresponds to the inner diameter $d_1$ in the front-rear direction, and connects front portions 66 (66*a*, 66*b*) on an inner surface of the elastic member 6, is smaller than the inner diameter d1.

The second rim 64 is within the third portion 48 in the present embodiment. The second rims 64 are engaged by the second receiving portions 480, respectively. Therefore, the elastic member 6 is hardly detached from the insertion portion 45 even when a forward force is applied to the elastic member 6.

The elastic member 6 includes contracted portions 67 (67*a*, 67*b*). An inner diameter d4 connecting the contracted portions 67 (67*a*, 67*b*) is smaller than the inner diameter d2.

A length between end portions 461 (461*a*, 461*b*) of the first receiving portion 460 is larger than the inner diameter d1. A length between end portions 630 (630*a*, 630*b*) of the first rim 63 is approximately equal to a length between the end portions 461 (461*a*, 461*b*) of the first receiving portion 460. In addition, the length of the first rim portion 46 in the front-rear direction is approximately equal to the length of the first rim 63 in the front-rear direction. Therefore, the first rim 63 contacts the first receiving portion 460 and fits into the first portion 46 when the elastic member 6 is inserted into the insertion portion 45. The medical personnel can set the elastic member 6 at an appropriate position inside the insertion portion 45 by inserting the elastic member 6 into the insertion portion 45 such that the first rim 63 contacts the first receiving portion 460. The second rim portion 64 is configured to contact the second receiving portion 480 when the elastic member 6 is inserted into the insertion portion 45.

Figure 5:
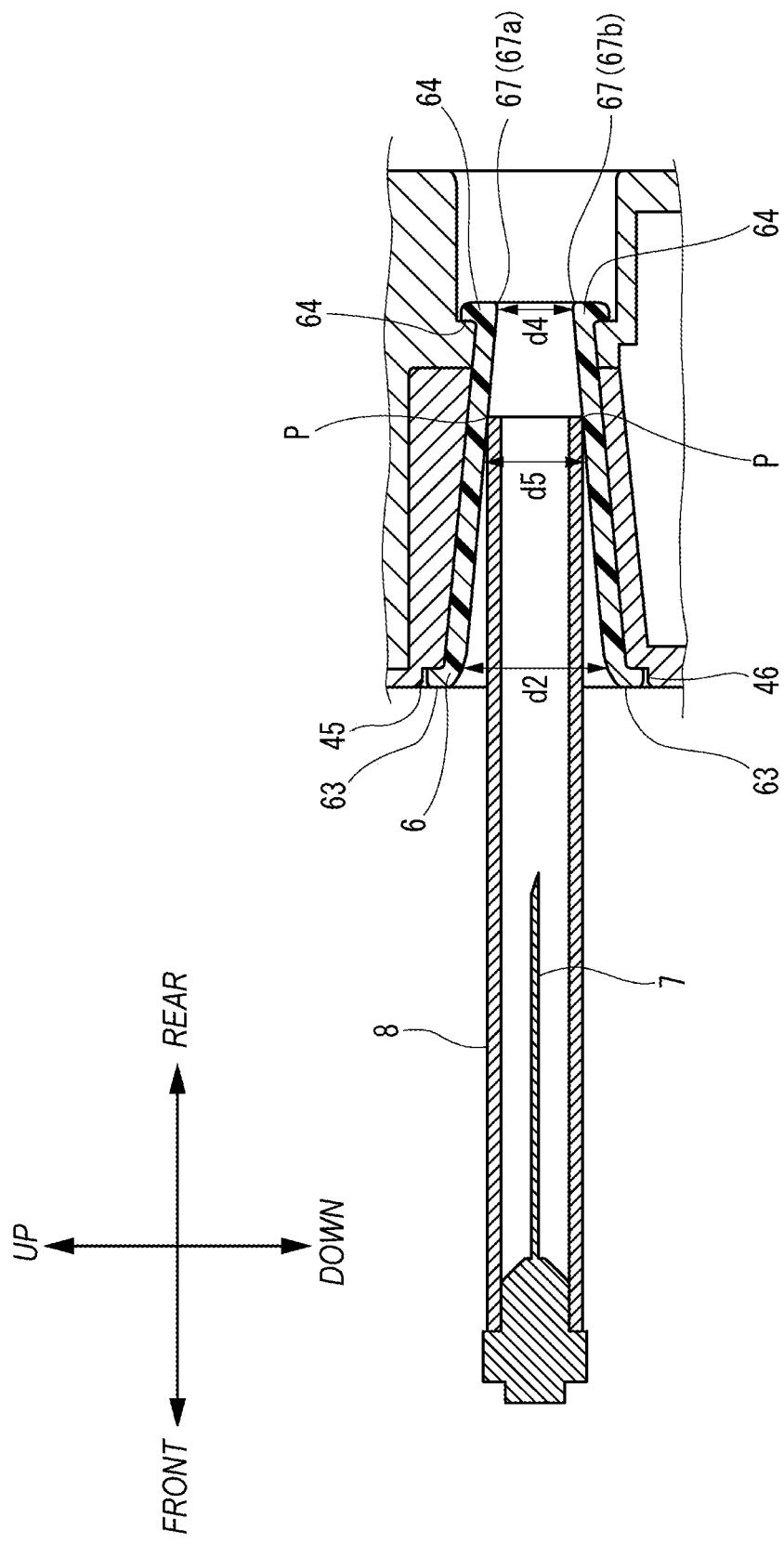
FIG. 5 is another cross-sectional view taken along the line IV-IV in FIG. 2, illustrating a cap being mounted on a needle electrode and held by the elastic member.

FIG. 5 is another cross-sectional view illustrating a cap 8 being mounted on the needle electrode 7 and held by the elastic member 6. The cap 8 protects the needle electrode 7. The medical personnel covers the needle electrode 7 with the cap 8. As illustrated in FIG. 5, the cap 8 mounted on the needle electrode 7 is inserted into the elastic member 6 from the front toward the rear. In the present embodiment, an outer diameter d5 of the cap 8 is smaller than the inner diameter d2, and is larger than the inner diameter d4.

As described above, the diameter of the tubular body 60 of the elastic member 6 is reduced rearward. Therefore, when the cap 8 is inserted into the elastic member 6 rearward, the cap 8 is held at a position P at which a diameter of the tubular body 60 is slightly smaller than the outer diameter d5 of the cap 8. The elastic member 6 is formed of an elastic material such as silicone. Accordingly, the cap 8 can be inserted into the elastic member 6 without being damaged even if the cap 8 is formed of a material such as a resin material.

The elastic member 6 deforms in a vicinity of the position P when the cap 8 is inserted into the elastic member 6. Therefore, the cap 8 is firmly held, by an elastic restoring force of the elastic member 6, in the vicinity of the position P. In addition, the elastic member 6 is formed of an elastic material, so that the medical personnel can also easily take out the cap 8 from the elastic member 6 when the cap 8 is taken out from the elastic member 6.

As described above, the medical personnel can easily squeeze the second opening portion 62 by applying a force toward the inside of the second opening portion 62 to the second rim 64 of the elastic member 6. Therefore, when the medical personnel desires to take out the elastic member 6 from the insertion portion 45, the elastic member 6 can be taken out from the insertion portion 45 by inserting a tool such as tweezers from the third portion 48 so as to grip the second rim and applying a force in the front direction to the elastic member 6 (a first method.).

The medical personnel can also take out the elastic member 6 by using a tool such as tweezers so as to grip the first rim 63 and applying a force in the rear direction to the elastic member 6 (a second method.). In the present embodiment, however, the slit 65 is formed in the second opening portion 62, so that the elastic member 6 can be taken out from the insertion portion 45 more easily by using the first method, compared with using the second method.

The medical personnel regularly cleans the elastic member 6 to keep it clean. According to the present embodiment, the cap 8 in the elastic member 6 is easy to taken out from the insertion portion 45. Accordingly, the medical personnel can take out the elastic member 6 from the insertion portion 45 and clean the cap 8, as necessary.

With the measuring apparatus 1 and the input box 4 having the configuration described above, the insertion portion 45 is configured such that the elastic member 6 is insertable into the insertion portion 45, and the elastic member 6 is configured to hold the cap 8 to be mounted on the needle electrode 7. More specifically, to hold the cap 8, the tubular elastic member 6 includes the contracted portion 67 having a smaller inner diameter than the entrance side. With this configuration, the electrode cap 8 can be held irrespective of its shape.

With the insertion portion 45 being a through hole, the medical personnel can take out the elastic member 6 from the insertion portion 45 by pulling the elastic member 6 out from the opening portion on one side of the insertion portion 45. The medical personnel can also push the elastic member 6 from the opening portion at the front side of the insertion portion 45 and pull the elastic member 6 out of the opening portion at the rear side of the insertion portion 45, for example. Therefore, it is easier to take out the elastic member 6.

With the above configuration, the elastic member 6 can firmly hold the cap 8 mounted on the needle electrode 7 in balanced manner.

With the elastic member 6 having the engagement portions 63*a* and 64*a* that can be engaged with the insertion portion 45 of the measuring apparatus 1, the elastic member 6 inserted inside the insertion portion 45 can be prevented from dropping out of the insertion portion 45.

With the first rim 63 being provided at the entrance of the elastic member 6, the medical personnel can set the elastic member 6 at an appropriate position with respect to the insertion portion 45.

With the first rim 63 of the elastic member 6 being received at the first receiving portion 460 provided at the end portion of the insertion portion 45, the medical personnel can set the elastic member 6 at an appropriate position with respect to the insertion portion 45.

With the second rim 64 being provided at an end portion of the elastic member 6 opposite to the entrance, when a pulling force toward the entrance side is applied to the elastic member 6 at the time of taking the needle electrode 7 out from the elastic member 6, the second rim 64 prevents the elastic member 6 from being detached from the insertion portion 45.

Further, at least one of the entrance of the elastic member 6 and the end portion of the elastic member 6 opposite to the entrance has a slit 65. Accordingly, the elastic member 6 can be easily taken out from the insertion portion by applying a force to a periphery of the slit 65.

As described above, it is easy to take out the elastic member 6. Therefore, the medical personnel can easily take out and clean the elastic member 6 as necessary.

In the example described above, the cap 8 is mounted on the needle electrode 7. However, the electrode on which the cap 8 is mounted may be an electrode other than the needle electrode, for example, a disk electrode.

In the example described above, the cap 8 has a linear shape when viewed in cross section. Alternatively, the cap 8 may have a nonlinear shape when viewed in cross section. The cap 8 may have a tubular shape, a square shape, or a polygonal shape such as a star shape.

In the example described above, the reduction ratio of the inner diameter of the second portion 47 is substantially the same as the reduction ratio of the outer diameter of the tubular body 60. However, this is a non-limiting example. For example, the reduction ratio of the inner diameter of the second portion 47 may be smaller than the reduction ratio of the outer diameter of the tubular body 60.

In the example described above, the insertion portion 45 is a through hole. However, the insertion portion 45 is not limited to a through hole. For example, the rear side of the insertion portion 45 may be closed. Even in this case, the medical personnel can take out the elastic member 6 from the front of the insertion portion 45 by using an instrument such as tweezers so as to grip the first rim 63 of the elastic member 6 and applying a force in the front direction to the elastic member 6.

In the example described above, the insertion portion 45 for the needle electrode is provided in the input box 4. However, this is a non-limiting example. The insertion portion 45 for holding the cap 8 may be provided in a structure in which the main unit 10 and the input box 4 are integrated.

In the example described above, as shown in FIG. 3, the outer diameter of the tubular body 60 of the elastic member 6 gradually decreases toward the rear. However, this is a non-limiting example. For example, the outer diameter of the tubular body 60 of the elastic member 6 may increase toward the rear from the front side of the elastic member 6 to a certain point, and may decrease further toward the rear from this point to the contracted portion 67.

The shape of the tubular body 60 of the elastic member 6 is symmetrical in the up-down direction when viewed from the side, but the shape is not limited to such a line-symmetric shape. For example, the tubular body 60 may have a shape in which the outline on the upper side is inclined downward and rearward, and the outline on the lower side is parallel to the outline on the upper side along the front-rear direction when viewed from the side. In addition, the tubular body 60 may have a shape in which the outline on the lower side is inclined upward and rearward, and the outline on the upper side is parallel to the outline on the lower side along the front-rear direction, when viewed from the side. The outline of the tubular body 60 when viewed from the side is not limited to a straight line, and may be partially or entirely curved.

In the example described above, the first receiving portion 460 is provided at the first portion 46 of the insertion portion 45. However, this is a non-limiting example. The elastic member 6 may be fixed to the input box 4 in a state in which the first receiving portion 460 is not provided at the first portion 46 of the insertion portion 45 and the first rim 63 of the elastic member 6 is in contact with a front surface of the input box 4.

While the presently disclosed subject matter has been described with reference to certain embodiments thereof, the scope of the presently disclosed subject matter is not limited to the embodiments described above, and it will be understood by those skilled in the art that various changes and modifications may be made therein without departing from the scope as defined by the appended claims.

What is claimed is:

1. A measuring apparatus configured to be connected to an electrode to measure biopotential, the measuring apparatus comprising:
    a tubular elastic member configured to hold a cap to be mounted on the electrode; and
    an insertion portion configured such that the elastic member is insertable into the insertion portion,
    wherein the tubular elastic member comprises an entrance having a first inner diameter, a contracted portion having a second inner diameter smaller than the first inner diameter, and a lumen extending between the entrance and the contracted portion, said lumen having a diameter that decreases between the entrance and the contracted portion, and
    wherein the cap is to be held by the lumen.

2. The measuring apparatus according to claim 1, wherein the elastic member further comprises an engagement portion configured to be engageable with the insertion portion in a state in which the elastic member is inserted inside the insertion portion.

3. The measuring apparatus according to claim 2, wherein the engagement portion comprises a first rim extending radially outward at the entrance of the elastic member.

4. The measuring apparatus according to claim 3, wherein the insertion portion comprises a receiving portion configured to receive the first rim at an end portion of the insertion portion.

5. The measuring apparatus according to claim 2, wherein the engagement portion comprises a second rim extending radially outward at an end portion of the elastic member opposite to the entrance.

6. The measuring apparatus according to claim 1, wherein the insertion portion comprises a through hole.

7. The measuring apparatus according to claim 1, wherein the elastic member further comprises a tapered surface over an entire circumference of the elastic member.

8. The measuring apparatus according to claim 1, wherein at least one of the entrance of the elastic member and an end portion of the elastic member opposite to the entrance comprises a slit.

9. An elastic member having a tubular shape and configured to hold a cap that protects an electrode used with a measuring apparatus,
    wherein the tubular elastic member comprises an entrance having a first inner diameter, a contracted portion having a second inner diameter smaller than the first inner diameter, and a lumen extending between the entrance and the contracted portion, said lumen having a diameter that decreases between the entrance and the contracted portion, and
    wherein the cap is to be held by the lumen.

10. The elastic member according to claim 9, further comprising a first rim extending radially outward at the entrance of the elastic member.

11. The elastic member according to claim 9, further comprising a second rim extending radially outward at an end portion of the elastic member opposite to the entrance.

12. The elastic member according to claim 9, further comprises a tapered surface over an entire circumference of the elastic member.

13. An input box configured such that an electrode used with a measuring apparatus is connected to the input box, the input box comprising:

a tubular elastic member configured to hold a cap to be mounted on the electrode; and an insertion portion configured such that the elastic member is insertable into the insertion portion, wherein the tubular elastic member comprises an entrance having a first inner diameter, a contracted portion having a second inner diameter smaller than the first inner diameter, and a lumen extending between the entrance and the contracted portion, said lumen having a diameter that decreases between the entrance and the contracted portion, and wherein the cap is to be held by the lumen.

* * * * *